March 26, 1974 H. KERRIGAN Plant Pat. 3,531
AZALEA PLANT
Filed Oct. 18, 1971
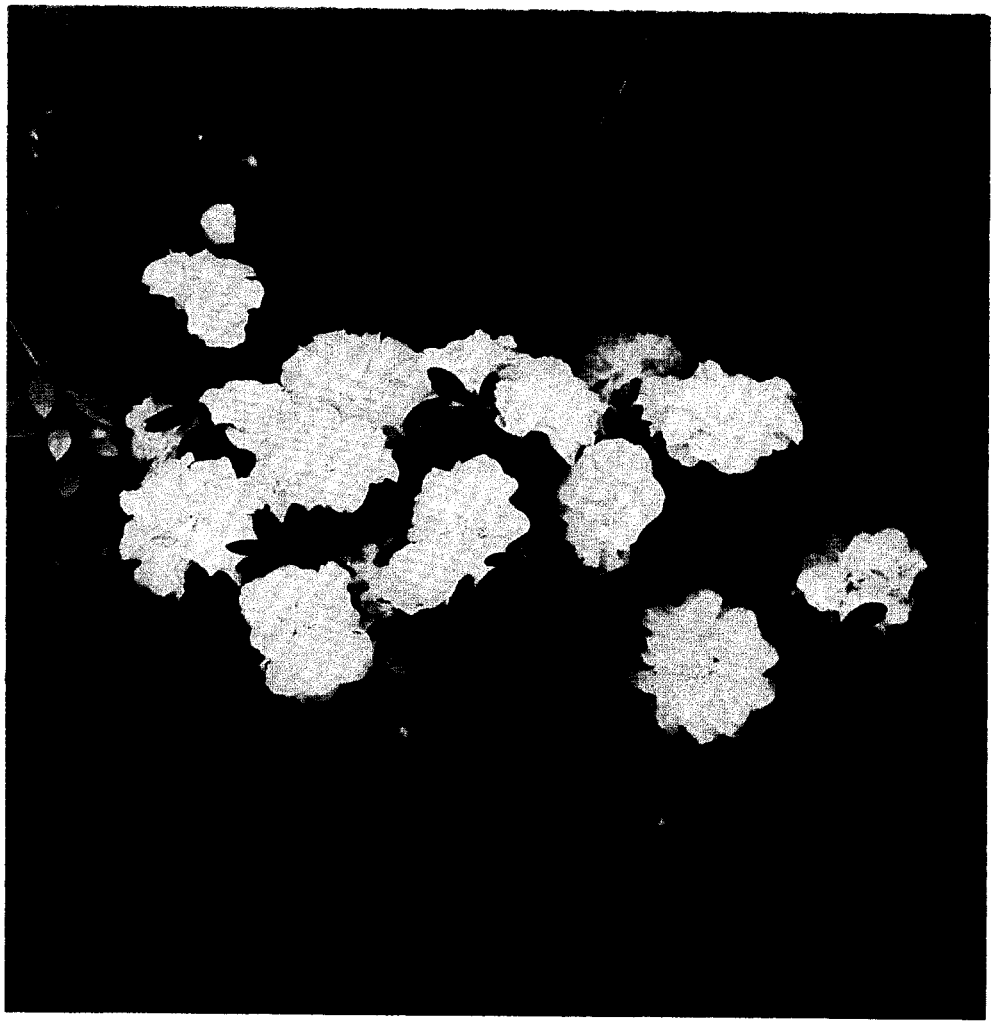

United States Patent Office

Plant Pat. 3,531
Patented Mar. 26, 1974

3,531
AZALEA PLANT

Howard Kerrigan, 24249 2nd St.,
Hayward, Calif. 94541

Filed Oct. 18, 1971, Ser. No. 190,238
Int. Cl. A01h 5/00
U.S. Cl. Plt.—55 1 Claim The invention relates to a new and distinct variety of azalea plant of the Belgian-Indica type, originated by me in 1956 as a consequence of a breeding program begun in 1943. The parentage of my new azalea plant is as follows: Blushing Bride (unpatented), the seed parent × Gables Rosebud (unpatented), the pollen parent.

The object of the cross was to produce a late flowering plant with more vigor and more double bloom than Blushing Bride and larger flowers than Rosebud. These objectives were achieved along with other desirable improvements, as evidenced by the following unique combination of characteristics which are outstanding in the new variety and which distinguish it from its parents as well as from all other varieties of which I am aware. My new variety is primarily characterized by: a combination of unusually long lasting, double ruffled blooms borne profusely on a vigorous, compact plant with a blooming season much later than other double florist type azaleas.

Asexual reproduction of my new variety by cutting, through a series of annual propagations at Oakland and Hayward, Calif., shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of one, two, and three year old flowering plants at Hayward, Oakland, and Santa Rosa, Calif.;

The plant is robust, vigorous, densely compact spreading to rounded, becoming 2–3′ across by 18–24″ high at maturity. The branches are stout but supple, gently arching. The basal shoots are vigorous, about 3/32″ in diameter. The axillary branches are about 1/16″ the first season. The internodes of basal shoots are between 3/8–1/2″ long. The stems are erect to prostrate; Lettuce Green (861/3) when young, becoming rufous at the base, to gray-brown when old. The bark is more or less conspicuously striate, with young stems bearing prominent hyaline, chestnut to brown strigae. The hyaline and tan strigae are found mainly on terminal growth, while the darker strigae occur on the basal portions of the shoots and the older wood.

The foliage is evergreen, and of two size classes. The leaves of vigorous growth are about 1–1 1/4″ long x 5/8–3/4″ wide, petiolate, the petioles are about 1/4″ long, the lamina is elliptic, decurrent, descending the petiole up to 3/32″. The leaf margins are entire, somewhat ciliate. The cilia are small, inconspicuous, and chestnut in color. The leaf apexes are acute, the midrib of the leaf is pubescent, especially below. The trichomes are flat, lanceolate, slender, up to 1/16″ in length, conspicuous, hyaline to chestnut, abutment on lower surface, smaller and sparser on upper surface of the midrib. The lamina is equally sparsely pubescent on both surfaces. The leaves of branches of older or more mature wood are smaller, about 7/8–3/4″ x 1/4–7/16″ wide with proportionally smaller trichomes, but otherwise similar to the larger leaves. The color of the leaves is Spinach Green (HCC 0960) above and below.

The bud of the inflorescence is Lettuce Green (HCC 861/3). The bud scales are small, about 1/4″ wide x 3/8″ long, heart shaped to lanceolate, becoming cucullate at anthesis. Pubescence is moderate to heavy, small, dark brown, essentially restricted to the rib. The scales become scarious with subhyaline margins and green apices at dehiscence.

The inflorescence is 1–3 flowered. The flowers are borne in an umbellate corymb. One flower of each of the three flowered inflorescences tends to mature at the same time, the other two maturing several days later. The peduncle of all flowers are of equal length. They are short, slender, 7/16″ long x 1/16″ in diameter, pubescent, light green. The pubescence is moderate to dense, hyaline to chestnut, short and silky. The calyx is somewhat petalaceous and somewhat expanded, five lobed, the sepals are entire or somewhat incised. The tube of the calyx is about 3/16″ deep x 3/8″ across. The lobes are about 1/4″ wide x 5/16″ long, ovate, quite uniform as to shape and size. The margins of the lobes are long, ciliate, as are the reverse. The cilia are hyaline to chestnut. The calyx color is white overlain with Lettuce Green (HCC 861/3). The corolla is very showy, white on both reverse and obverse becoming lightly streaked on the reverse of the tube with Lettuce Green (HCC 861/4). The inner surface of the tube is overlain and freckled with Lettuce Green (HCC 861/3), particularly on the dorsal three lobes. The tube is about 3/8″ long x 5/8″ wide at the throat, flaring, bilaterally symmetrical, slightly gibbous, somewhat higher than broad, more or less prominently fluted with the midveins depressed.

The corolla may be imperfect with the sinuses of the lobes extending to the base. The five corolla lobes are of two size classes. The ventral two larger about 7/8″–1″ across x 7/8″–1″ long. The dorsal three lobes are smaller, about 3/4–7/8″ across x 3/4–7/8″ deep. The flower is about 2 1/8–2 1/4″ across x 7/8–1 1/8″ deep.

The flower is totally double, with all of the stamens petalaceous. There are two size classes of staminodes. The smaller are 3–7 in number, adnate to the corolla, and from about 3/16 to 1/4″ wide by 1/4 to 5/16″ long. The larger are unusually large, and often lobed, the lobes imbricate. There are from 5–8 large staminodes of which half or more are lobed. The entire petalodes are about 3/8 to 1/2″ wide by 3/4–1″ long. The lobed petalodes are about 1 1/2 to 2 1/4″ wide by 3/4 to 1″ long. The lobes measure 3/4 to 1″ wide by 1–1 1/8″ long.

The pistil is deformed and completely variable; it is multi-styled and green in color, with many of the styles fused. The average length is 1/4″. The thickened basal portion of the styles is pubescent. The pubescene is long, silky, and hyaline. The ovary is about 3/32″ long x 1/16″ wide, and heavily pubescent. The pubescence is dense, long, silky, and hyaline.

Having thus disclosed my invention, I claim:

1. A new and distinct variety of azalea plant of the Belgian-Indica type substantially as herein shown and described primarily characterized by: a combination of unusually long lasting double ruffled blooms borne profusely on a vigorous, compact plant with a blooming season much later than other double florist type azaleas.

No references cited.

ROBERT E. BAGWILL, Primary Examiner